US012708530B2

(12) United States Patent
Didrick

(10) Patent No.: US 12,708,530 B2
(45) Date of Patent: Aug. 18, 2026

(54) DIGIT PROSTHESIS ASSEMBLY

(71) Applicant: Daniel Didrick, Mead, CO (US)

(72) Inventor: Daniel Didrick, Mead, CO (US)

(*) Notice: Subject to any disclaimer, the term of this patent is extended or adjusted under 35 U.S.C. 154(b) by 1005 days.

(21) Appl. No.: 17/947,146

(22) Filed: Sep. 18, 2022

(65) Prior Publication Data

US 2023/0093422 A1 Mar. 23, 2023

Related U.S. Application Data

(60) Provisional application No. 63/245,296, filed on Sep. 17, 2021.

(51) Int. Cl.
*A61F 2/58* (2006.01)
*A61F 2/78* (2006.01)
*A61F 2/50* (2006.01)

(52) U.S. Cl.
CPC ................ *A61F 2/586* (2013.01); *A61F 2/78* (2013.01); *A61F 2002/5038* (2013.01); *A61F 2002/587* (2013.01); *A61F 2002/7862* (2013.01); *A61F 2220/0091* (2013.01)

(58) Field of Classification Search
CPC ...... A61F 2/586; A61F 2/78; A61F 2002/587; A61F 2002/7862; A61H 1/0288
See application file for complete search history.

(56) References Cited

U.S. PATENT DOCUMENTS 12,011,376 B2 * 6/2024 Pulver ........................ A61F 2/80
2022/0296391 A1 * 9/2022 Popovic .................. A61F 2/586
2023/0026300 A1 * 1/2023 Zhang .................. A61H 1/0288
2023/0093422 A1 * 3/2023 Didrick .................. A61F 2/586
623/64

* cited by examiner

*Primary Examiner* — Bruce E Snow
(74) *Attorney, Agent, or Firm* — Leyendecker & Lemire, LLC

(57) ABSTRACT

A digit prosthesis assembly is described. Embodiments of the digit prosthesis assembly include, but are not limited to, an attachment assembly, a thumb assembly, one or more finger assemblies, a pinky finger assembly, a palm engagement assembly, and combinations thereof.

19 Claims, 7 Drawing Sheets

DIGIT PROSTHESIS ASSEMBLY

CROSS-REFERENCE TO RELATED APPLICATION

This application claims the benefit of U.S. Provisional Application No. 63/245,296, filed Sep. 17, 2021.

BACKGROUND

Prosthetics for digits are well known. Digit prosthetics can range from very complicated neuroprosthetics to very simple mechanical prosthetics. For many years, anaplastologists have attempted to add a functional aspect to their passive silicone non-bending fingers for finger amputees. Although they look incredibly realistic, they do not move or bend in any way. An aesthetic finger that cannot accept much force is acceptable for some, having additional stability and strength is also a needed feature for others.

A digit prosthesis device that can be implemented to mimic and/or replace an amputated digit is needed.

DETAILED DESCRIPTION

Figure 1:
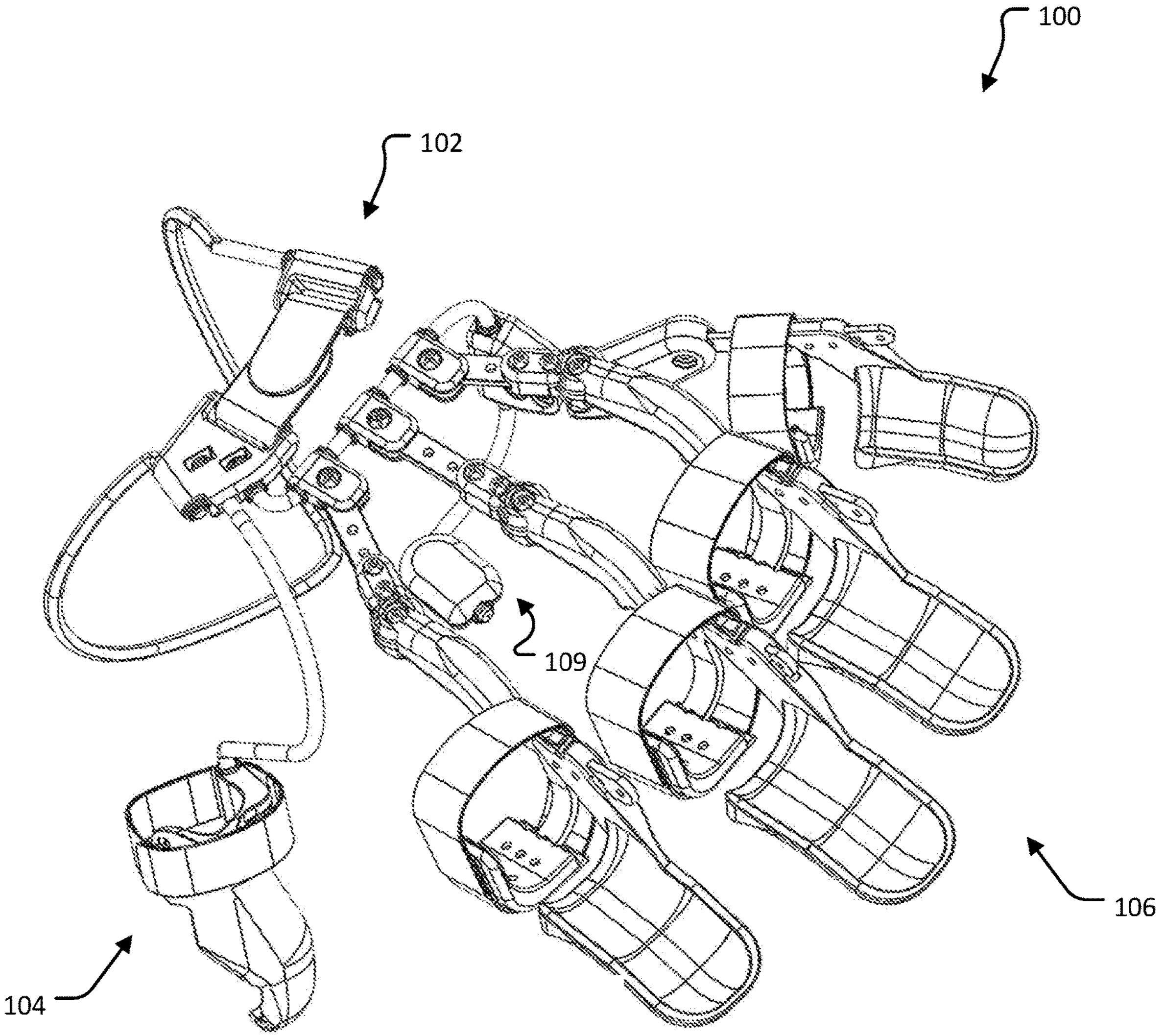
FIG. 1 is a perspective view of a digit prosthesis assembly according to one embodiment of the present invention.

Embodiments of the present invention include a digit prosthesis assembly that can be implemented to mimic and/or protect one or more digits on a hand. The digit prosthesis assembly can implement a plurality of different hinge mechanisms depending on the digit to be mimicked/protected. For example, a novel hinge design can be implemented to mimic a movement of a thumb. In another example, a novel hinge design can be implemented to mimic a finger movement and provide a pain free interaction between the digit prosthesis assembly and a hand of a user.

Embodiments of the present invention can further include one or more adjustable protective digit covers that can eliminate unwanted pressure from being exerted on sensitive areas of an injured digit (e.g., a finger or a thumb). The prosthesis device can divert pressure on targeted areas of an injured finger and can provide a benefit for partial finger (and partial thumb) amputees. A user can adjust the digit cover to redirect pressure exerted on one area of the finger to another area when grasping or lifting objects. For example, if someone has an injured fingertip, the finger cover can transfer pressures exerted on the fingertip back near the base of the finger. In another example, when an injury near the base of the finger needs protection from unwanted pressure, the device can transfer pressure to the tip of the finger. For example, an inner surface of the digit cover that makes contact with the injured finger (or thumb) can be adjusted by changing a distance between the digit cover and the injured digit.

In some embodiments, an articulated artificial finger assembly, as disclosed in U.S. Pat. No. 6,908,489, can be implemented with the digit prosthesis assembly. U.S. Pat. No. 6,908,489 is hereby incorporated by reference in its entirety. In other embodiments, a locking mechanism prosthetic finger, as disclosed in Japanese Publication JP2020074991, can be implemented with the digit prosthesis assembly. Japanese Publication JP2020074991 is hereby incorporated by reference in its entirety.

In one embodiment, the digit prosthesis assembly can include, but is not limited to, an attachment assembly, a first digit (or thumb) assembly, a second digit (or index finger) assembly, a third digit (or middle finger) assembly, a fourth digit (or ring finger) assembly, a fifth digit (or pinky finger) assembly, and a palm engagement assembly. The first digit assembly can be removably coupled to the attachment assembly. The second to fifth digit assemblies can be removably coupled to the palm engagement assembly. The palm engagement assembly can be coupled to the attachment assembly. The attachment assembly can be implemented to secure the digit prosthesis assembly to a wrist (or arm) of a user.

The thumb assembly can include a thumb cover (or thumb prosthesis) and an extension member rotatably coupled to the attachment assembly. The extension member and the attachment assembly can form a hinge for the thumb assembly. The thumb cover can be configured to extend past the metacarpal joint of the thumb to a desired length of the user. Typically, the thumb cover can end where a thumb would end and run along an inside of the space between the thumb and fingers and resting near the metacarpal joint of the thumb. Of note, when pressure is exerted on any area of the thumb cover, the pressure is not placed on the thumb, as would be normal, but rather can be transferred back to where the extension member may be in contact with the metacarpal joint of the thumb and the metacarpal joint can receive all of the pressure. As can be appreciated, the rotating hinge of the thumb assembly can enable a curve in the extension member to adjust a rotational dexterity of the thumb cover. A distal end of the extension member can connect to a compatibly configured thumb cover that can act as a protective shell for the thumb to ensure contact is not made with any area the user wishes to protect from pressure (or can act as an artificial thumb when no thumb is present).

The thumb assembly can be configured to rotate with a thumb providing the thumb cover proximate the thumb as the thumb is moved from a flat position to proximate a palm of the user. Of significant note, the thumb can be distanced from the thumb cover to ensure that no pressure is felt by an upper portion of the thumb. As previously mentioned, the thumb assembly can redirect pressure from an upper portion of the thumb to approximate the metacarpal joint of the thumb. The thumb assembly can provide protection to the thumb by directing pressure (e.g., from the pinky finger engaging the thumb cover) to approximate the metacarpal joint of the thumb, allowing the thumb to move freely in relation to the thumb cover when the thumb cover is pressed against an object.

In one embodiment, the digit prosthesis assembly can include an extension member with a rotating hinge that can attach to a hinge member of the attachment assembly located on a dorsal side of the hand. For the thumb, the extension member can extend from a dorsal side of the hand to the palmar side between the thumb and pointer finger of a user. A distal end of the extension member can rotate back and forth along a substantially circular arc to simulate the movement of a fully functional thumb.

The digit prosthesis assembly can implement two different hinge designs for the fingers. Of note, the finger hinges primary movement can allow the fingers to flex and extend at the metacarpal joint in a different but equally novel manner to the thumb hinge. Both hinge designs can be used to replicate the movement of the metacarpal joints of the fingers and can be interchanged. Although interchangeable, a first hinge may have benefits when compatibly configured to the 2nd or 5th digits (e.g., when the hinge can be lined up directly beside the metacarpal joint of the finger without interfering with another finger). A second hinge can include a curved hinge that can rotate around the metacarpal joint of a finger in a controlled manner, simulating a pivot point located at a center of the curved hinge.

The first hinge can generally be used for the 5th digit (i.e., pinky finger) as the first hinge can line a fastener between a hinge member and the attachment assembly (e.g., a pivot point) up with the metacarpal joint as the hinge assembly can sit proximate to the pinky finger metacarpal joint.

The curved hinge (or second hinge) can offer a novel way to simulate the movement of a joint despite having the hinge sit outside of the hand. When replacing an amputated finger, (or covering an injured finger where the hinge must be placed between two fingers) the curved hinge can allow a curved hinge member to move along a curved keyway inside a housing. The curved hinge member and the curved keyway can thereby simulate a hinge with a pivot point in the center of an arc of the curved hinge member.

In one embodiment, the digit prosthesis assembly can include an attachment assembly and a thumb assembly. The attachment assembly can be secured to a wrist of a user and the thumb assembly can be rotatably coupled to the attachment assembly. The thumb assembly can be implemented to protect an injured thumb and/or mimic an amputated thumb. The thumb assembly can include a thumb cover and a curved extension member. A first end of the curved extension member can be rotatably secured to the attachment assembly and a second end can be secured to the thumb cover. The curved extension member can be contoured to an area of a hand between the thumb and the index finger.

In another embodiment, the digit prosthesis assembly can include an attachment assembly, a thumb assembly, a palm engagement assembly, and one or more finger assemblies. One or more of the finger assemblies can include a curved hinge design allowing for a natural movement of a finger. At least one of the finger assemblies can include a straight hinge design. The palm engagement assembly can be implemented to stabilize the digit prosthesis assembly when one or more of the finger assemblies are implemented.

One embodiment of the digit prosthesis assembly can include, but is not limited to, an attachment assembly and a thumb assembly. The attachment assembly can be adapted to be removably coupled to a wrist of a user. The thumb assembly can include, but is not limited to, an extension member and a thumb member. The extension member can have a substantially "U" shape. The thumb member can be coupled to a second end of the extension member. A first end of the extension member can be adapted to be located on a dorsal side of a hand of the user. The first end can also be rotatably coupled to the attachment assembly. The second end of the extension member can be adapted to be located underneath a metacarpal joint of a thumb of a user.

One embodiment of the digit prosthesis assembly can include, but is not limited to, an attachment assembly and a thumb assembly. The attachment assembly can be adapted to be removably coupled to a wrist of a user. The thumb assembly can include, but is not limited to, an extension member and a thumb member. The thumb member can be coupled to a second end of the extension member. A first end of the extension member can be rotatably coupled to the attachment assembly. The second of the extension member can be adapted to be located underneath and approximate a thenar eminence or a metacarpal joint of a thumb of a user.

Another embodiment of the digit prosthesis assembly can include the previously mentioned attachment assembly, the thumb assembly, and further a palm engagement assembly, a first finger assembly, and a second finger assembly. The palm engagement assembly can be coupled to the attachment assembly and can be adapted to interface with a palm of the user. The first finger assembly can include, but is not limited to, a first finger attachment assembly, a hinge member, and a first finger cover. The first finger attachment assembly can be adapted to couple to the palm engagement assembly. The hinge member can have a first end rotatably coupled to the attachment assembly. The first finger cover can be coupled to a second end of the hinge member. The second finger assembly can include, but is not limited to, a second finger attachment assembly, a curved hinge member, and a second finger cover. The second finger attachment assembly can be adapted to couple to the palm engagement assembly. The curved hinge member can have a first end slidably engaging the second finger attachment assembly. The second finger cover can be coupled to a second end of the curved hinge member.

Embodiments of the present invention further includes artificial finger segments designed to move similarly to a user's prior finger when bending at a metacarpal joint. The previously described hinge assemblies are unique as the hinge assemblies are configured to sit on a surface of a user's hand but can mimic the movement of the finger which has a joint located inside the hand. As previously mentioned, a rotational thumb hinge can offer additional dexterity compared to other prosthetic thumbs previously released that simply flex on a linear plane. The rotational hinge mechanism offers a realistic movement that can have both a passive or active function prosthetic thumb attached. The previously disclosed finger and thumb covers can be connected to the hinge assemblies offering a rigid protective covering which transfers forces being applied to the fingers to a less sensitive or uninjured part of the user's hand. As can be appreciated, the previously disclosed hinge assemblies can offer a benefit to both anaplastologists who wish to integrate additional function into their passive devices as well as functional finger manufacturers who seek additional dexterity for their devices utilizing our disclosed retention methods and novel hinges.

Terminology

The terms and phrases as indicated in quotation marks (" ") in this section are intended to have the meaning ascribed to them in this Terminology section applied to them throughout this document, including in the claims, unless clearly indicated otherwise in context. Further, as applicable, the stated definitions are to apply, regardless of the word or phrase's case, to the singular and plural variations of the defined word or phrase.

The term "or" as used in this specification and the appended claims is not meant to be exclusive; rather the term is inclusive, meaning either or both.

References in the specification to "one embodiment", "an embodiment", "another embodiment, "a preferred embodiment", "an alternative embodiment", "one variation", "a variation" and similar phrases mean that a particular feature, structure, or characteristic described in connection with the embodiment or variation, is included in at least an embodiment or variation of the invention. The phrase "in one embodiment", "in one variation" or similar phrases, as used in various places in the specification, are not necessarily meant to refer to the same embodiment or the same variation.

The term "couple" or "coupled" as used in this specification and appended claims refers to an indirect or direct physical connection between the identified elements, components, or objects. Often the manner of the coupling will be related specifically to the manner in which the two coupled elements interact.

The term "directly coupled" or "coupled directly," as used in this specification and appended claims, refers to a physical connection between identified elements, components, or objects, in which no other element, component, or object resides between those identified as being directly coupled.

The term "approximately," as used in this specification and appended claims, refers to plus or minus 10% of the value given.

The term "about," as used in this specification and appended claims, refers to plus or minus 20% of the value given.

The terms "generally" and "substantially," as used in this specification and appended claims, mean mostly, or for the most part.

Directional and/or relationary terms such as, but not limited to, left, right, nadir, apex, top, bottom, vertical, horizontal, back, front and lateral are relative to each other and are dependent on the specific orientation of a applicable element or article, and are used accordingly to aid in the description of the various embodiments and are not necessarily intended to be construed as limiting.

An Embodiment of a Digit Prosthesis Assembly

Referring to FIG. 1, a detailed diagram of an embodiment 100 of a digit prosthesis assembly for use with a hand are illustrated. The digit prosthesis assembly 100 can be implemented to protect and/or mimic the five digits of a hand. Of note, the digit prosthesis assembly device 100 can be configured to be implemented with 1-5 digits of a hand and any combinations thereof. FIG. 1 includes a perspective view of the digit prosthesis assembly 100.

As shown in FIG. 1, the digit prosthesis assembly 100 can include, but is not limited to, an attachment assembly 102, a thumb assembly 104, a plurality of finger assemblies 106, and a palm engagement assembly 109. The attachment assembly 102 can be implemented to secure the digit prosthesis assembly 100 to a wrist of a user. The thumb assembly 104 can be implemented to provide a protective cover and/or mimic a thumb for a thumb amputee. The finger assemblies 106 can be implemented to protect and/or mimic one of the four finger digits. As will be discussed hereinafter, the finger assemblies 106 can include an assembly configured for a pinky finger and an assembly configured for the pointer finger, middle finger, and ring finger. The palm engagement assembly 109 can typically be implemented when at least one finger assembly 106 is included. Of note, embodiments are contemplated with (i) the attachment assembly 102 and the thumb assembly 104, (ii) the attachment assembly 102, the palm engagement assembly 109, and one or more of the finger assemblies 106, and (iii) the attachment assembly 102, the thumb assembly 104, the palm engagement assembly 109, and one or more of the finger assemblies 106.

Of note, each of the finger assemblies 106 and the thumb assembly 104 can be configured to secure to a digit (or partial digit) via a fastening mechanism (e.g., a hook and loop closure strap). The finger assemblies 106 and the thumb assembly 104 can be adjusted to determine where on a finger or thumb protection is provided. For instance, a portion of a cover can be adjusted in relation to the finger (or thumb) to dictate where protection is provided. As can be appreciated, the cover can thereby offer a gap between the injured part of the finger and an inner surface of the cover while allowing direct contact between the inner surface of the cover and an area of the finger that is uninjured. The digit prosthesis assembly 100 can be implemented to apply pressure without pain being exerted on the injured area of a finger.

Figure 2A:
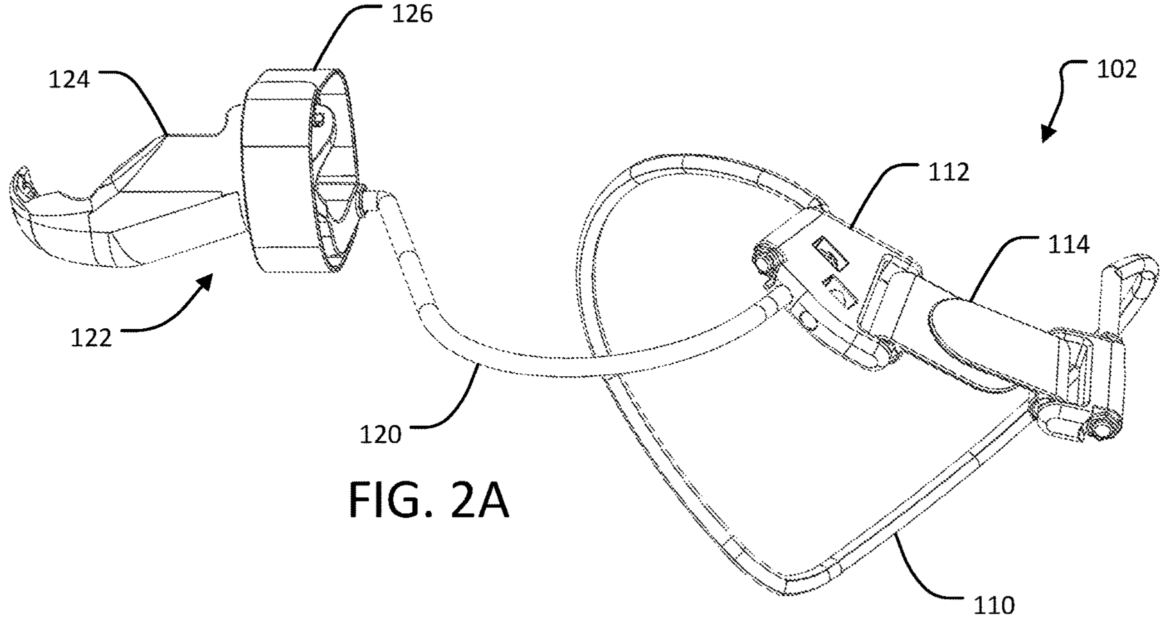
FIG. 2A is a perspective view of a digit prosthesis assembly according to one embodiment of the present invention.
Figure 2B:
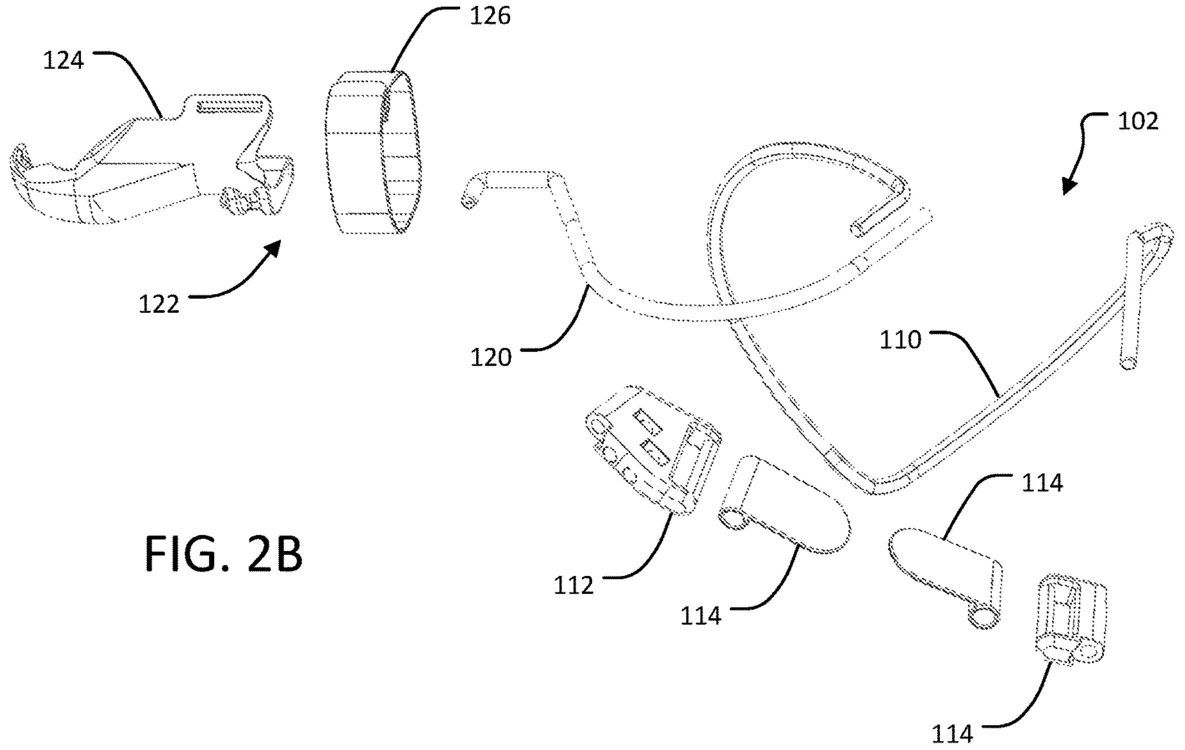
FIG. 2B is an exploded view of a digit prosthesis assembly according to one embodiment of the present invention.

Referring to FIGS. 2A-2B, detailed diagrams of an embodiment of the digit prosthesis assembly 100 including the attachment assembly 102 and the thumb assembly 104 are illustrated. FIG. 2A includes a perspective view of the thumb assembly 104 in combination with the attachment assembly 102. FIG. 2B includes an exploded view of FIG. 2A.

The attachment assembly 102 can include, but is not limited to, a wrist member 110, a hinge member 112, and an attachment member 114. A first end of the wrist member 110 can be coupled to the hinge member 112 and a second end of the wrist member 110 can be coupled to the attachment member 114. The wrist member 110 can be configured to go around a wrist with the hinge member 112 and the attachment member 114 being located on a top of the wrist. The wrist member 110 can generally be manufactured from a semi-rigid (or rigid) material. The hinge member 112 can be configured to couple to the thumb assembly 104. The attachment member 114 can include a means for securing the attachment assembly 102 to a user. In one instance, the attachment member 114 can include a pair of hook and loop strips configured to removably couple to one another. In another instance, the attachment member 114 can include a pliable strap configured to mate with a protrusion. Typically, the hinge member 112 can include a portion of the attachment member 114. For example, a first hook and loop strip can be secured to the attachment member 114 and a second hook and loop strip can be secured to the hinge member 112.

As shown, the thumb assembly 104 can include, but is not limited to, an extension member 120 and a thumb member 122. When the digit prosthesis assembly 100 may be attached to a user, the extension member 120 can generally extend from the hinge member 112, located on a dorsal side of a hand to between a metacarpal bone of a thumb and a metacarpal one of an index finger of the user to an underside of the thumb. The thumb member 122 can be implemented to protect a thumb of a user and/or simulate a thumb for a thumb amputee. Typically, the thumb member 122 can include a cover 124 and a digit strap 126. The digit strap 126 can be implemented to secure the thumb cover 124 proximate a digit of a user. In one instance, a cover can be implemented to ensure an injured thumb can interact with an object without applying pressure to the injured portion. In another instance, the thumb member 122 can include a thumb prosthetic for a thumb amputee.

A first end of the extension member 120 can rotatably couple to the hinge member 112 of the attachment assembly 102 and a second end can attach to the thumb member 122. Generally, the extension member 120 can rotate about a longitudinal axis of the first end of the extension member 120. In one example embodiment, the first end of the extension member 120 can be threaded and can insert into the hinge member 112 where the threaded end can be threadably coupled to a nut within the hinge member 112. Of note, the threads can allow for the extension member 120 to rotate in relation to the hinge member 112. The extension member 120 can rotate in relation to the attachment assembly 102 allowing the thumb cover 124 to move with a thumb in a natural movement.

In one example, as shown in FIG. 2B, the second end of the extension member 120 can have a generally "U" shape. In such a configuration, the second end of the extension member 120 can be in the same plane as the rest of the extension member 120. As can be appreciated, the second end illustrated in FIG. 2B is meant for illustrative purposes only and is not meant to be limiting. Of note, a variety of different means for securing the thumb cover 124 to the second end of the extension member 120 can be implemented without exceeding a scope of the present invention.

Figure 3A:
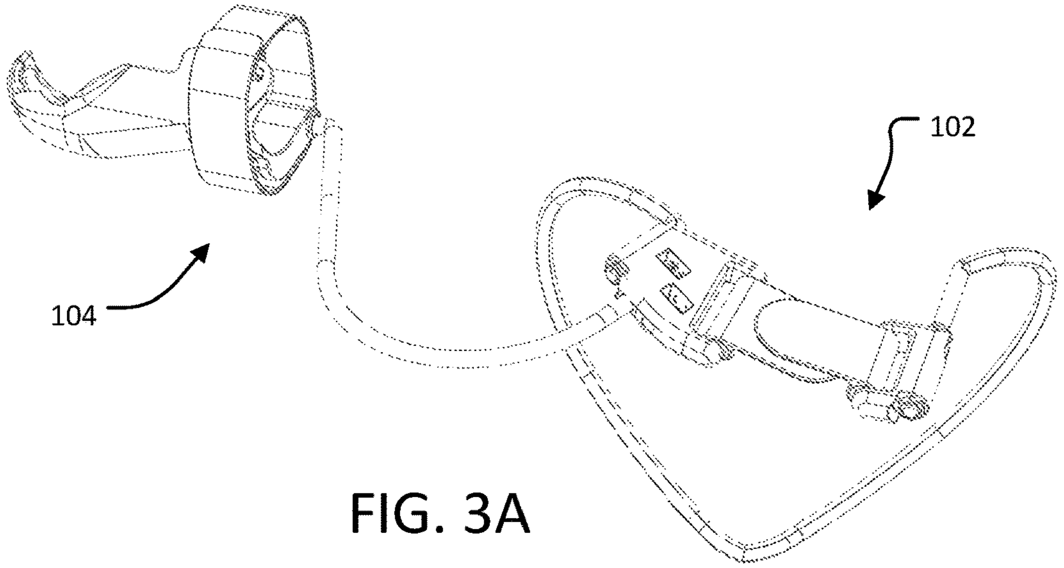
FIGS. 3A-3C include perspective views of a thumb assembly moving according to one embodiment of the present invention.
Figure 3B:
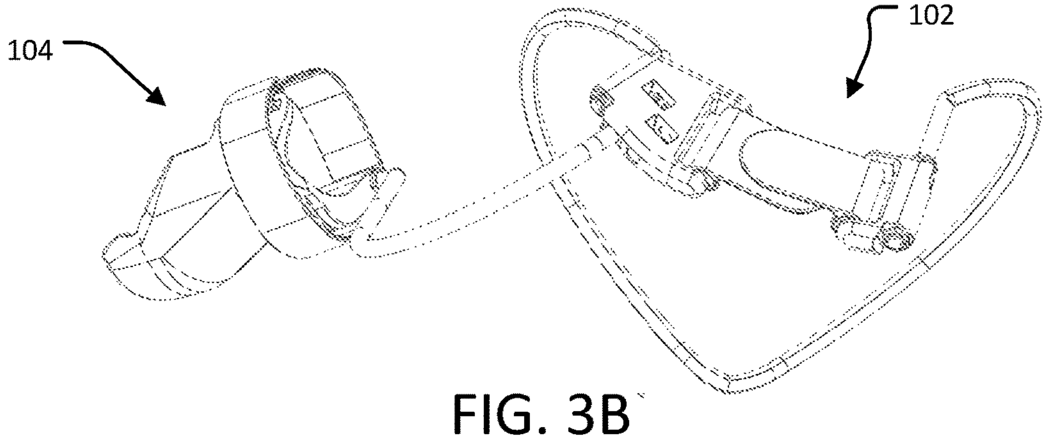
Figure 3C:
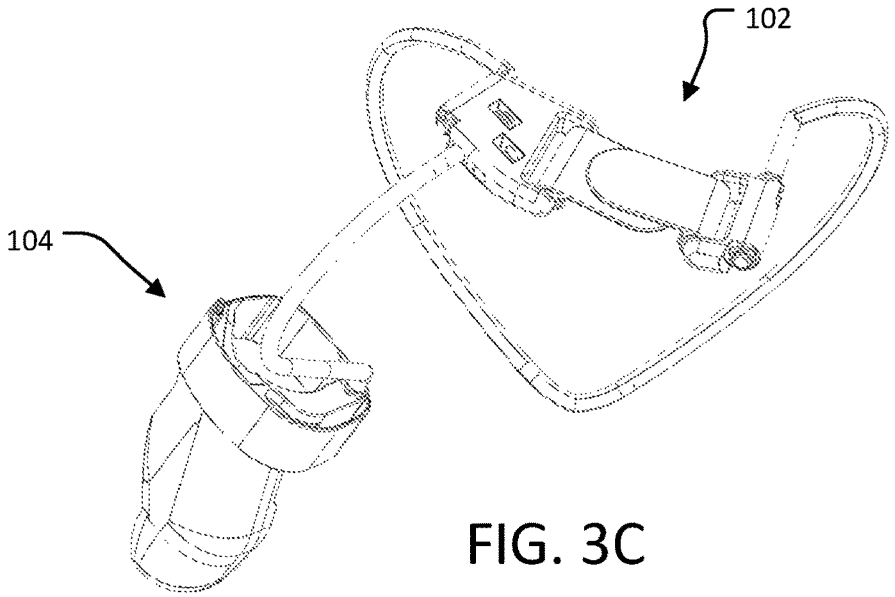

Referring to FIGS. 3A-3C, a partial movement of the thumb assembly 104 is illustrated. As shown, a curvature of the extension member 120 can allow the second end of the extension member 120 to rotate in a substantially circular motion and mimic the motion of the metacarpal joint of a thumb. Generally, when connected to a user, the thumb cover 124 can move back and forth along a circular arc to mimic a movement of a fully functional thumb. In one instance, the extension member 120 can be adapted to curve around a thumb web space of a user.

The extension member 120 can be curved to follow a curvature of a hand between the thumb and index finger. Typically, the extension member 120 can interface with the hand between the thumb and the index finger and allow for pressure on the thumb cover 124 to be transferred to the extension member 120. In some instances, a curvature of the extension member 120 can allow the extension member 120 to rotate around the metacarpal joint of the thumb.

The thumb cover 124 (or thumb prosthesis) can extend past the metacarpal joint of the user to a desired length. Typically, the thumb cover 124 can run along the inside of the space between the thumb and fingers and resting near the metacarpal joint of the thumb. Of note, when pressure is exerted on any area of the thumb cover 124, the pressure can be transferred back to where the extension member 120 is in contact with the metacarpal joint of the thumb and the metacarpal joint can receive all of the pressure. As can be appreciated, the rotating hinge (e.g., the extension member 120 and hinge member 112) of the thumb assembly 104 can enable the extension member 120 to adjust a rotational dexterity of the thumb cover 124.

Figure 3D:
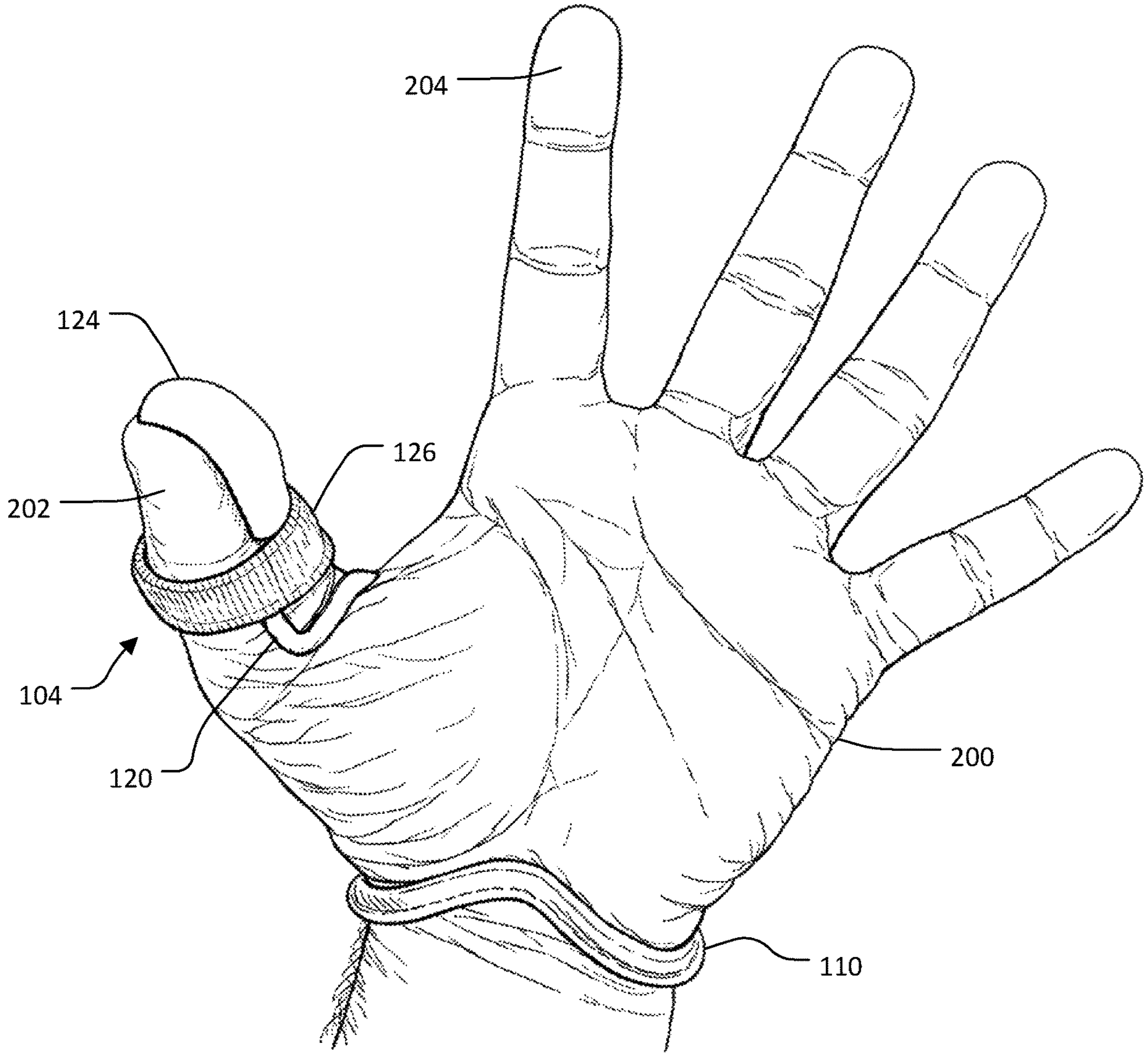
FIG. 3D includes a palmer side view of a thumb assembly interfacing with a hand according to one embodiment of the present invention.

Referring to FIG. 3D, a palmer side view of a hand 200 of a user and the thumb assembly 104 interfacing with the hand 200 is illustrated. As shown, the second end of the extension member 120 can be located approximate the metacarpal joint of a thumb 202 of the hand 200. Further, the extension member 120 is shown extending between the thumb 202 and a pointer finger 204.

Figure 4A:
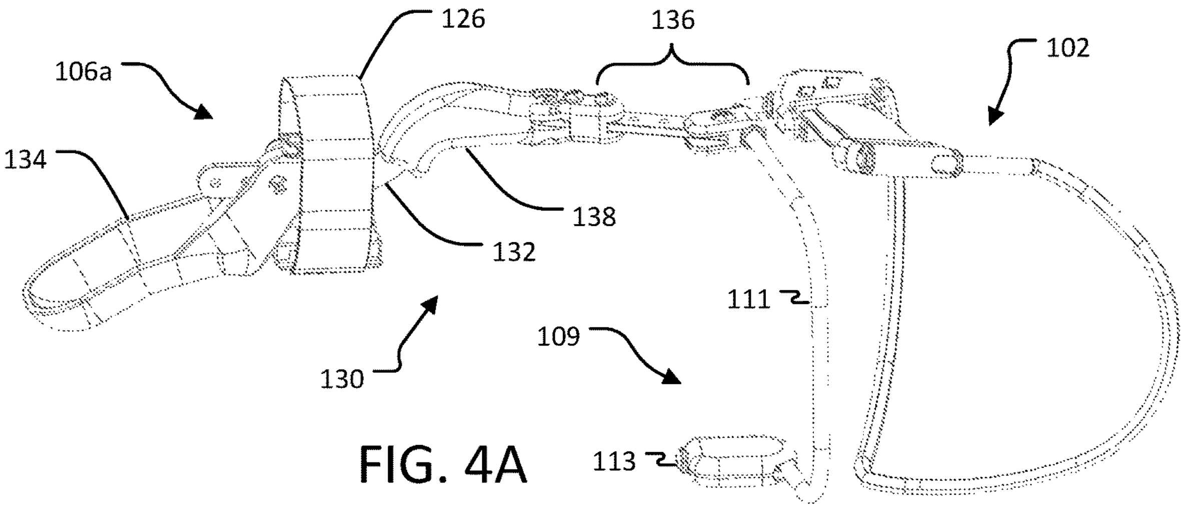
FIGS. 4A-4C include various views of a digit prosthesis assembly implementing a finger assembly having a first hinge configuration according to one embodiment of the present invention.
Figure 4B:
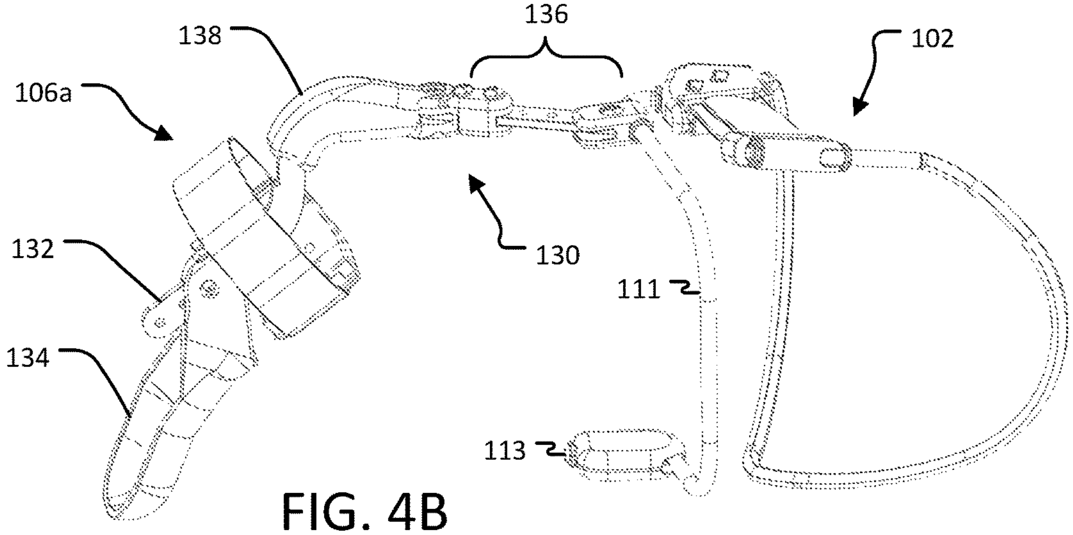
Figure 4C:
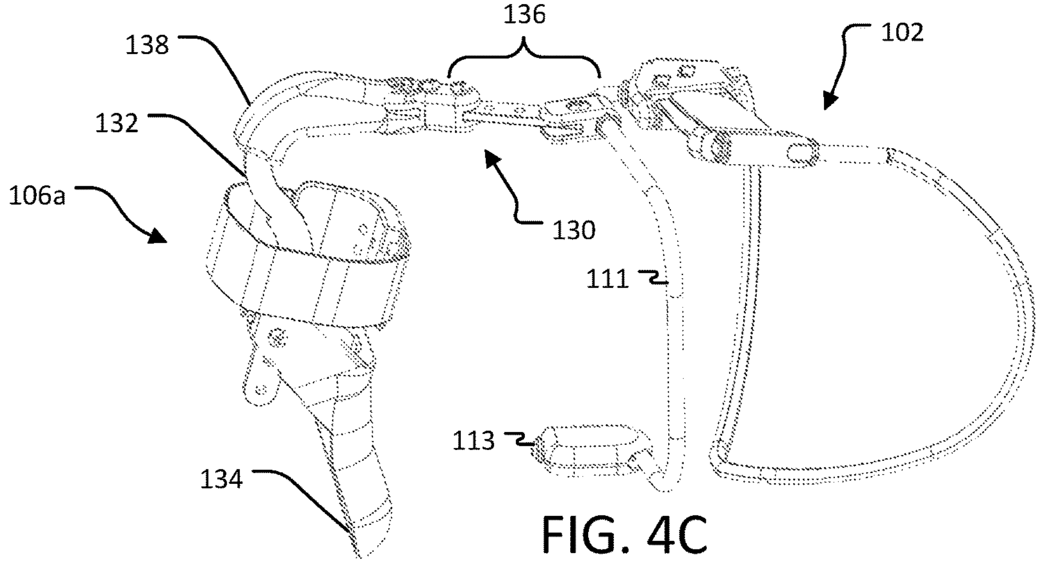

Referring to FIGS. 4A-4C, detailed diagrams of one embodiment of the digit prosthesis assembly 100 with a curved hinge finger assembly 106*a* and the attachment assembly 102 are illustrated. Of note, the curved hinge finger assembly 106*a* can typically be implemented with a pointer finger, a middle finger, and a ring finger.

In embodiments including one or more finger assemblies 106, the attachment assembly 102 can further include the palm engagement assembly 109 for interfacing with a palm of a user. The palm engagement assembly 109 can include an extension member 111 and an engagement member 113. The palm extension member 111 can have a first end coupled to the hinge member 112 of the attachment assembly 102 and a second end coupled to the palm engagement member 113. The palm extension member 111 can include a curved portion to extend around from a top of a hand, from the hinge member 112, down and around to a palm of the hand. The palm engagement assembly 109 can be implemented to push against a palm of a user when a finger assembly 106 may be actuated. In one instance, a first end of the palm extension member 111 can be coupled to the attachment assembly 102 and can extend from the attachment assembly 102 around an ulnar edge to a palmar side of a hand of a user. The engagement member 113 can be coupled to a second end of the palm extension member 111 and can be located proximate a palmar side of the hand of the user.

The curved hinge finger assembly 106*a* can include, but is not limited to, a finger attachment assembly 130, a curved hinge member 132, and a finger cover (or finger prosthetic) 134. The finger attachment assembly 130 can extend out from the palm extension member 111 and can include an extension member 136 and a housing 138 having a keyway (not shown). The extension member 136 can typically include a means for coupling to the palm extension member 111 and a means for coupling to the housing 138. In some instances, the curved hinge member 132 can include one or more holes for receiving a fastener therein to secure the finger cover 134 to the curved hinge member 132. A location of the finger cover 134 in relation to a finger of the user can be adjusted. Of note, the finger cover 134 can be moved to adjust which part of the finger may be protected.

The keyway in the housing 138 can be configured to receive the curved hinge member 132. The curved hinge member 132 can move in and out of the housing 138 via the keyway. As the finger cover 134 may be moved upwards, the curved hinge member 132 can slide further into the keyway. As the finger cover 134 may be moved down, the curved hinge member 132 can slide out of the keyway while remaining stable within the keyway when moving within a range of motion of a finger. The curved hinge member 132 in combination with the keyway in the housing 138 can simulate a natural movement of a finger. More specifically, the curved hinge member 132 can rotate around a metacarpal joint simulating a pivot point located at a center of the curved hinge member 132. Similar to the thumb cover 124, the finger cover 134 can include a digit strap 126 to secure the finger cover 134 to a digit of a user.

Since the curved hinge finger assembly 106*a* can be configured to work on an exterior of a hand, a rigid structure that can mimic the movement of a human finger is needed where the joint is located in the hand. The curved hinge member 132 can slide freely within the keyway of the housing 138. As can be appreciated, the keyway can be curved as well. The curved keyway can hold the curved hinge member 132 in place by only allowing the curved hinge member 132 to move in and out along a path of the keyway. Of significant note, the curved hinge assembly 106*a* can simulate a more common hinge where a pivot point would be in a center of the curved hinge member 132. However, because a normal pivot point for a finger is located inside of a hand, the curved hinge member 132 allows the finger cover 134 to move more closely in-line with a controlling finger.

Figure 5A:
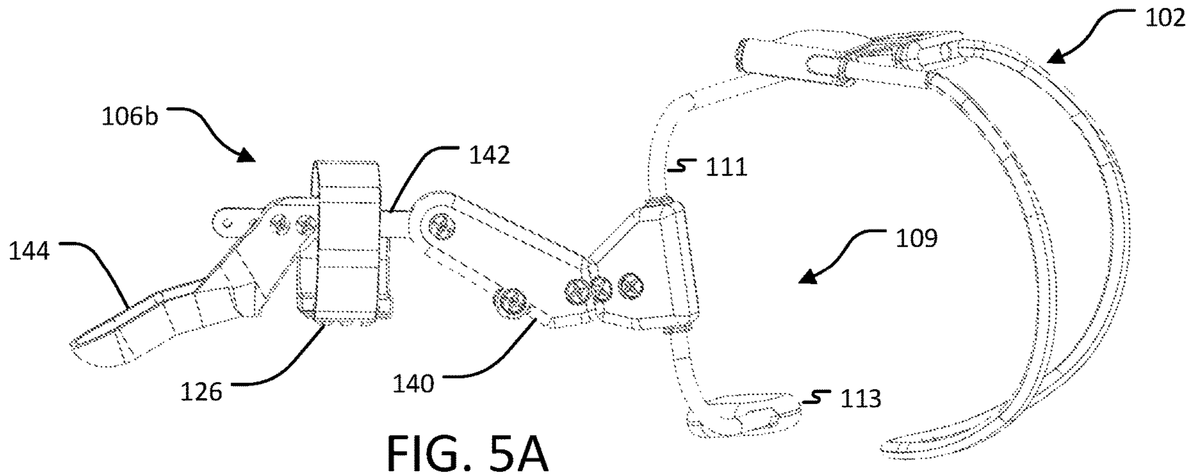
FIGS. 5A-5C include various views of a digit prosthesis assembly implementing a finger assembly having a second hinge configuration according to one embodiment of the present invention.
Figure 5B:
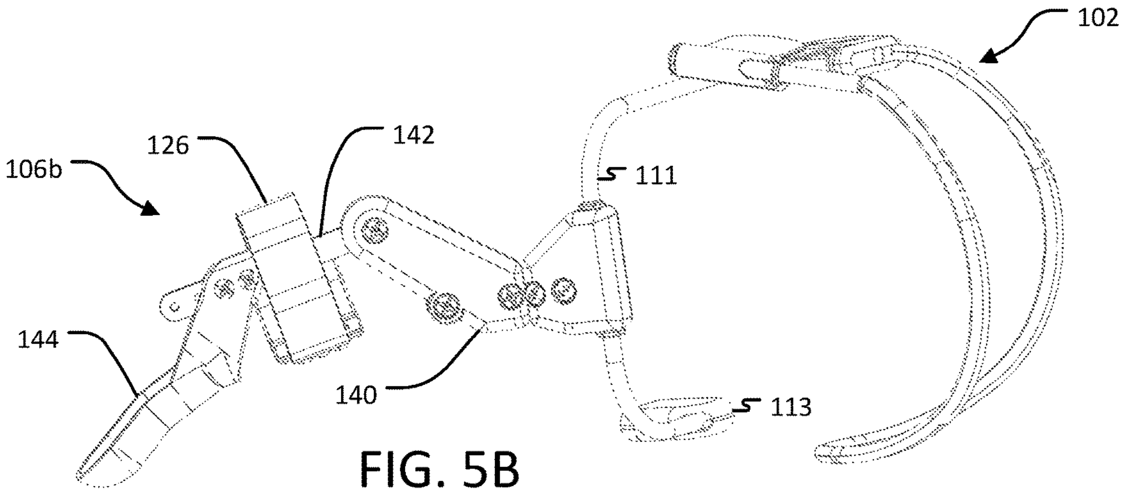
Figure 5C:
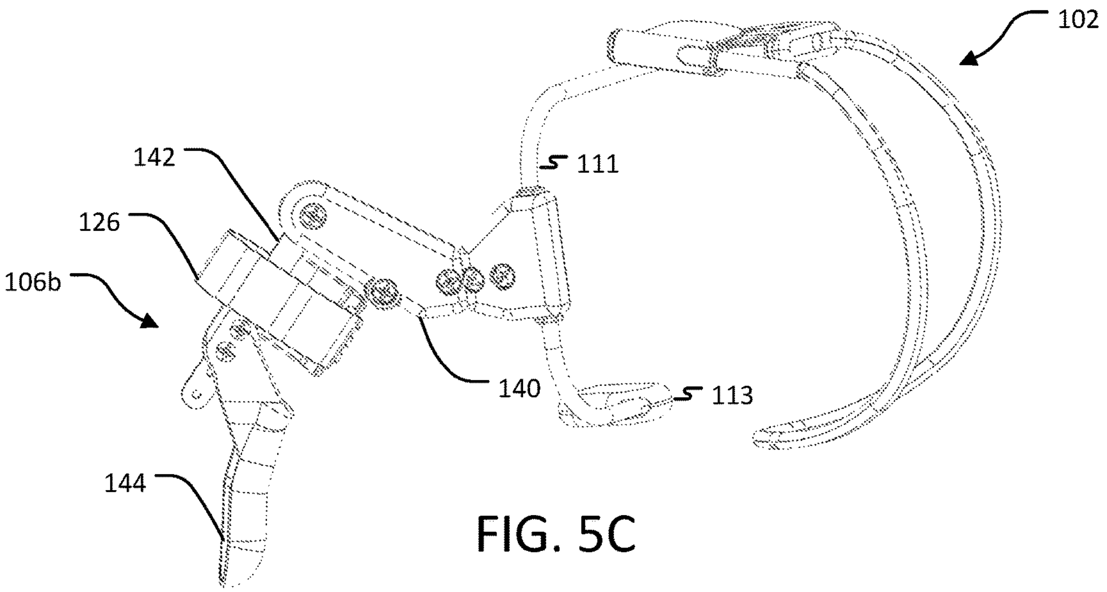

Referring to FIGS. 5A-5C, detailed diagrams of an embodiment of the digit prosthesis assembly 100 including a pinky finger assembly 106*b* in combination with the attachment assembly 102 are illustrated. The pinky finger assembly 106*b* can typically be implemented with the pinky finger. It is to be appreciated, that the pinky finger assembly 106*b* can be implemented with other fingers. Of note, the pinky finger assembly 106*b* can typically be coupled to the extension member 111 of the palm engagement assembly 109.

As shown, the pinky finger assembly 106*b* can include, but is not limited to, a finger attachment assembly 140, a hinge member 142, and a finger cover 144. A first end of the hinge member 142 can be rotatably coupled to a distal end of the finger attachment assembly 140. The finger cover 144 can be coupled to a second end of the hinge member 142. In some instances, the hinge member 142 can include one or more holes for receiving a fastener therein to secure the finger cover 144 to the hinge member 142. Of note, the finger cover 144 can be moved to adjust which part of the finger may be protected. For instance, a location of the finger cover 144 can be adjusted in relation to a finger of the user. Similar to the thumb cover 124, the finger cover 144 can include a digit strap 126 to secure the finger cover 144 to a digit of a user.

The pinky finger assembly 106*b* can be placed next to a metacarpal joint of a pinky finger of a user. As can be appreciated, by being able to place the pinky finger assembly 106*b* proximate the metacarpal joint of the pinky finger, the pinky finger assembly 106*b* can mimic the movement of the pinky finger metacarpal joint and a curved hinge may not be needed. The hinge member 142 can be a straight bar (or rod) that rotates on the finger attachment assembly 140, thereby moving the finger cover 144 that is attached to the hinged member 142 in an up and down movement.

Figure 6:
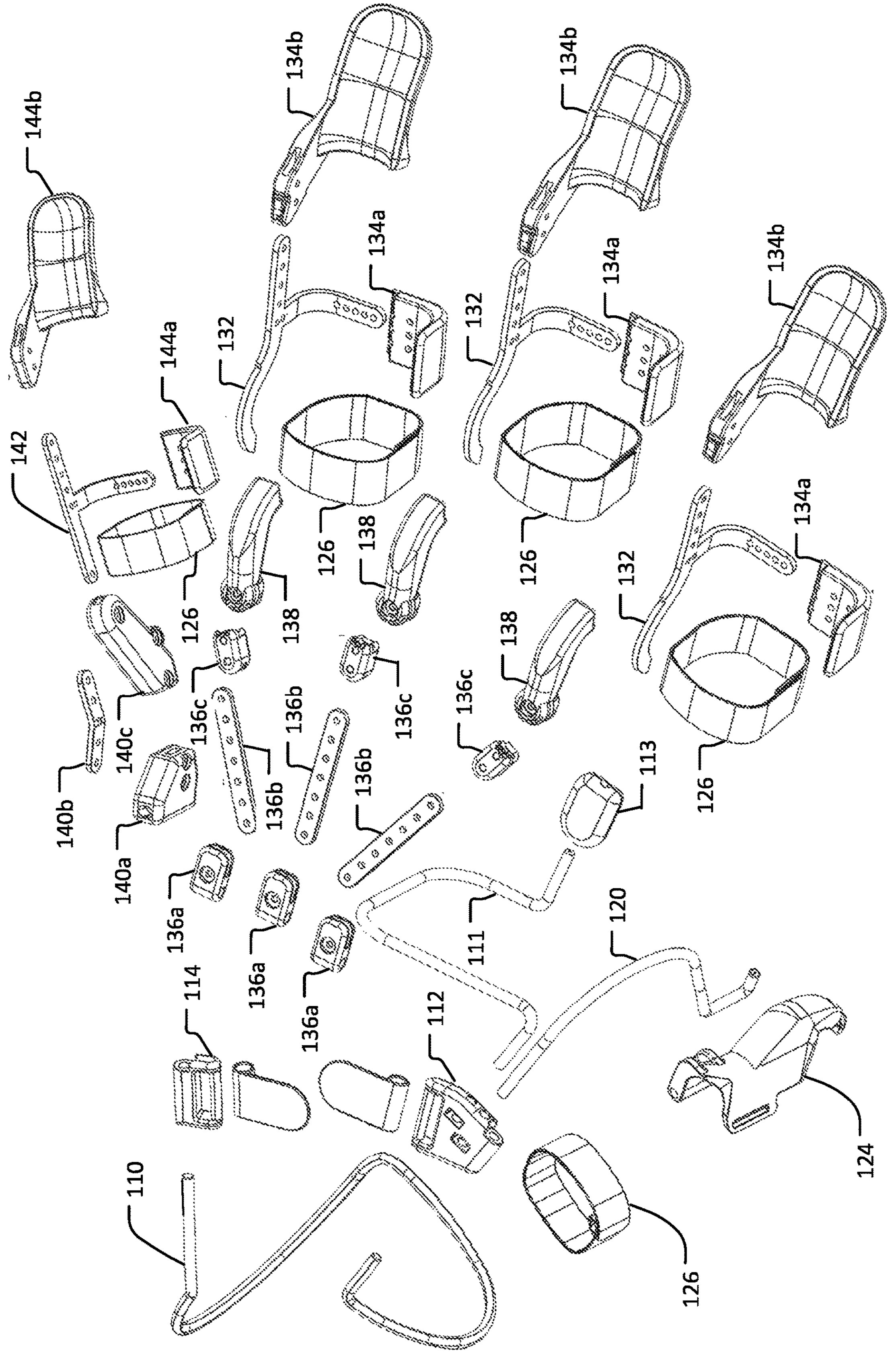
FIG. 6 is an exploded view of a digit prosthesis assembly according to one embodiment of the present invention.

Referring to FIG. 6, an exploded view of the digit prosthesis assembly 100 is illustrated. Of note, the finger cover 134, the extension member 136, the pinky finger attachment assembly 140, and the pinky finger cover 144 may each comprise a plurality of components. Generally, multiple components can be implemented to allow for adjustability to better fit a user of the digit prosthesis assembly 100.

In one example, the finger cover 134 can include a first member 134*a* and a second member 134*b*. As shown, the curved hinge member 132 can include attachment sections for the first member 134*a* and the second member 134*b*. A first attachment section for the first member 134*a* can extend out perpendicular to a plane of the curved hinge section and be located below the curved hinge and a second attachment section for the second member 134*b*. The first member 134*a* can be adjustably coupled to the first attachment section of the curved hinge member 132 and can be implemented to adjust a width of the finger cover 134. The second member 134*b* can be adjustably coupled to the second attachment section of the curved hinge member 132 and can be implemented to adjust a position of the finger cover 134 relative to a finger of a user. As shown, the second member 134*b* can be moved closer and further from the curved hinge section to adjust a longitudinal location of the finger cover 134.

In one example, the extension member 136 can include a first coupling 136*a*, a bar 136*b*, and a second coupling 136*c*. The first coupling 136*a* can couple to the palm extension member 111 and a first end of the bar 136*b*. Of note, the bar 136*b* can be pivotably coupled to the first coupling 136*a* such that the bar 136*b* can move laterally side-to-side. A second end of the bar 136*b* can coupled to the second coupling 136*c*. The second coupling 136*c* can couple to the housing 138. In some instances, the second coupling 136*c* and the housing 138 can be mated such that the housing 138 has a limited movement laterally side-to-side. Of note, a length of the bar 136*b* can be adjusted to a specific user.

The pinky finger attachment assembly 140 can include a first coupling 140*a*, a bar 140*b*, and a second coupling 140*c*. The first coupling 140*a* can be implemented to couple to the palm extension member 111. A first end of the bar 140*b* can couple to the first coupling 140*a* and a second end can couple to the second coupling 140*c*. The second coupling 140*c* can be implemented to couple to the straight hinge member 142. Of note, the straight hinge member 142 can rotatably couple to the second coupling 140*c* such that the straight hinge member 142 can rotate up and down around where the straight hinge member 142 couples to the second coupling 140*c*.

Similar to the finger cover 134, the pinky finger cover 144 can include a first member 144*a* and a second member 144*b*. The pinky finger hinge 142 can include a first attachment section of the first member 144*a* and a second attachment section for the second member 144*b*. The first attachment section for the first member 144*a* can extend out perpendicular to a plane of the straight hinge section and be located below the straight hinge and a second attachment section for the second member 144*b*. The first member 144*a* can be adjustably coupled to the first attachment section of the straight hinge member 142 and can be implemented to adjust a width of the finger cover 144. The second member 144*b* can be adjustably coupled to the second attachment section of the straight hinge member 142 and can be implemented to adjust a position of the finger cover 144 relative to a finger of a user. As shown, the second member 144*b* can be moved closer and further from the straight hinge section to adjust a longitudinal location of the finger cover 144.

Alternative Embodiments and Variations

The various embodiments and variations thereof, illustrated in the accompanying Figures and/or described above, are merely exemplary and are not meant to limit the scope of the invention. It is to be appreciated that numerous other variations of the invention have been contemplated, as would be obvious to one of ordinary skill in the art, given the benefit of this disclosure. All variations of the invention that read upon appended claims are intended and contemplated to be within the scope of the invention.

I claim:

1. A digit prosthesis assembly comprising:

an attachment assembly adapted to be removably coupled to a wrist of a user; and a thumb assembly including:

an extension member having a substantially "U" shape; and a thumb member coupled to a second end of the extension member;

wherein (i) a first end of the extension member is (a) adapted to be located on a dorsal side of a hand of the user, and (b) rotatably coupled to the attachment assembly; and (ii) the second end of the extension member is adapted to be located underneath a metacarpal joint of a thumb of a user.

2. The digit prosthesis assembly of claim 1, wherein the thumb member includes a thumb cover and a strap.

3. The digit prosthesis assembly of claim 1, wherein the thumb member includes a thumb prosthetic.

4. The digit prosthesis assembly of claim 1, wherein a portion of the extension member between the first end and the second end is adapted to pass between a metacarpal bone of a thumb and a metacarpal bone of an index finger of a user.

5. The digit prosthesis assembly of claim 1, wherein the extension member is adapted to curve around a thumb web space of a user.

6. The digit prosthesis assembly of claim 1, wherein a location of the thumb cover in relation to a thumb of a user is adjustable.

7. The digit prosthesis assembly of claim 1, wherein the extension member rotates about a longitudinal axis of the first end.

8. The digit prosthesis assembly of claim 1, wherein the attachment assembly includes:

a hinge member, the first end of the extension member adapted to rotatably couple to the hinge member;

an attachment member; and a wrist member having a first end connected to the attachment member and a second end connected to the hinge member.

9. The digit prosthesis assembly of claim 8, wherein the wrist member is adapted to wrap around a wrist of a user.

10. The digit prosthesis assembly of claim 1, the digit prosthesis assembly further including:

a palm engagement assembly coupled to the attachment assembly and being adapted to interface with a palm of the user; and at least one finger assembly including:

a finger attachment assembly adapted to couple to the palm engagement assembly;

a curved hinge member slidably engaging the finger attachment assembly; and a finger cover coupled to the curved hinge member.

11. A digit prosthesis assembly comprising:

an attachment assembly adapted to be removably coupled to a wrist of a user; and a thumb assembly including:

an extension member having at least one bend and being adapted to extend from a dorsal side of a hand of the user to a palmar side between a thumb and a pointer finger; and a thumb member coupled to a second end of the extension member;

wherein (i) a first end of the extension member is rotatably coupled to the attachment assembly; and (ii) the second end of the extension member is adapted to be located underneath and approximate a thenar eminence or a metacarpal joint of the thumb of the user.

12. The digit prosthesis assembly of claim 11, wherein pressure applied to the thumb member can be transferred to a section of the extension member adapted to be in contact with the user.

13. The digit prosthesis assembly of claim 11, wherein the thumb member includes a thumb cover and the second end of the extension member is adapted to be located approximate the metacarpal joint.

14. The digit prosthesis assembly of claim 11, wherein a curvature of the at least one bend of the extension member allows the second end of the extension member to rotate in a substantially circular motion.

15. The digit prosthesis assembly of claim 11, the digit prosthesis assembly further including:

a palm engagement assembly coupled to the attachment assembly and being adapted to interface with a palm of the user; and at least one finger assembly including:

a finger attachment assembly adapted to couple to the palm engagement assembly;

a hinge member having a first end rotatably coupled to the attachment assembly; and a finger cover coupled to a second end of the hinge member.

16. A digit prosthesis assembly comprising:

an attachment assembly adapted to be removably coupled to a wrist of a user;

a thumb assembly including:

an extension member having at least one bend; and a thumb member coupled to a second end of the extension member;

wherein (i) a first end of the extension member is (a) adapted to be located on a dorsal side of a hand of the user, and (b) rotatably coupled to the attachment assembly; and (ii) the second end of the extension member is adapted to be located underneath a metacarpal joint of a thumb of a user;

a palm engagement assembly coupled to the attachment assembly and being adapted to interface with a palm of the user;

a first finger assembly including:

a first finger attachment assembly adapted to couple to the palm engagement assembly;

a hinge member having a first end rotatably coupled to the attachment assembly; and a first finger cover coupled to a second end of the hinge member;

a second finger assembly including:

a second finger attachment assembly adapted to couple to the palm engagement assembly;

a curved hinge member having a first end slidably engaging the second finger attachment assembly; and a second finger cover coupled to a second end of the curved hinge member.

17. The digit prosthesis assembly of claim 16, the digit prosthesis assembly further including a third finger assembly being substantially similar to the second finger assembly and a fourth finger assembly being substantially similar to the second finger assembly.

18. The digit prosthesis assembly of claim 17, wherein the first finger assembly is adapted to interface with a fifth digit, the second finger assembly is adapted to interface with a fourth digit, the third finger assembly is adapted to interface with a third digit, and the fourth finger assembly is adapted to interface with a second digit.

19. The digit prosthesis assembly of claim 16, wherein the palm engagement assembly includes:

an extension member, a first end of the extension member being coupled to the attachment assembly and adapted to extend from the attachment assembly around an ulnar edge to a palmar side of a hand of a user; and an engagement member coupled to a second end of the extension member and adapted to be located proximate a palmar of the hand of the user.

* * * * *